(12) United States Patent
Greenberg et al.

(10) Patent No.: US 6,507,758 B1
(45) Date of Patent: Jan. 14, 2003

(54) LOGARITHMIC LIGHT INTENSIFIER FOR USE WITH PHOTORECEPTOR-BASED IMPLANTED RETINAL PROSTHETICS AND THOSE PROSTHETICS

(75) Inventors: Robert J. Greenberg, Los Angeles, CA (US); Abraham N. Seidman, Beverly Hills, CA (US); Joseph H. Schulman, Santa Clarita, CA (US)

(73) Assignee: Second Sight, LLC, Valencia, CA (US)

( * ) Notice: Subject to any disclaimer, the term of this patent is extended or adjusted under 35 U.S.C. 154(b) by 0 days.

(21) Appl. No.: 09/515,383

(22) Filed: Feb. 29, 2000

Related U.S. Application Data

(60) Provisional application No. 60/125,875, filed on Mar. 24, 1999.

(51) Int. Cl.⁷ .................................................. A61N 1/18
(52) U.S. Cl. ....................................................... 607/54
(58) Field of Search ........................... 607/53, 54, 116; 623/4.1, 6.63

(56) References Cited

U.S. PATENT DOCUMENTS

| | | |
|---|---|---|
| 4,628,933 A | 12/1986 | Michelson |
| 5,016,633 A | 5/1991 | Chow |
| 5,369,415 A | 11/1994 | Richard et al. |
| 5,397,350 A | 3/1995 | Chow et al. |
| 5,556,423 A | 9/1996 | Chow et al. |
| 5,659,327 A | 8/1997 | Furness, III et al. |
| 5,895,415 A | 4/1999 | Chow et al. |
| 5,935,155 A | 8/1999 | Humayun et al. |
| 5,957,958 A | 9/1999 | Schulman et al. |
| 6,230,057 B1 | 5/2001 | Chow et al. |
| 6,389,317 B1 * | 5/2002 | Chow et al. .................. 607/54 |

OTHER PUBLICATIONS

M. Schwarz, et al., "Hardware Architecture of a Neural Net Based Retina Implant for Patients suffering from Retinitis Pigmentosa", 1996 IEEE International Conference on Neural Networks.

Guyton, et al., "Theory and design of capacitor electrodes for chronic stimulation", Medical and Biological Engineering, Sep. 1974, p. 613–620.

Slinley & Wolbarsht, "*Safety with Lasers and Other Optical Sources: A Comprehensive Handbook*", Plenum Pub. Corp. (1980).

* cited by examiner

*Primary Examiner*—Jeffrey R. Jastrzab
(74) *Attorney, Agent, or Firm*—Scott Dunbar

(57) ABSTRACT

This invention is for directly modulating a beam of photons onto the retinas of patients who have extreme vision impairment or blindness. Its purpose is to supply enough imaging energy to retinal prosthetics implanted in the eye which operate essentially by having light (external to the eye) activating photoreceptors, or photo-electrical material. The invention provides sufficient light amplification and does it logarithmically. While it has sufficient output light power, the output light level still remains at a safe level. Most preferred embodiments of this invention provide balanced biphasic stimulation with no net charge injection into the eye. Both optical and electronic magnification for the image, as for example, using an optical zoom lens, is incorporated. Otherwise, it would not be feasible to zoom in on items of particular interest or necessity. Without proper adjustment, improper threshold amplitudes would obtain, as well as uncomfortable maximum thresholds. Therefore, to adjust for these, a way of proper adjustment for the threshold amplitudes and maximum comfortable thresholds is provided. Furthermore, to the extent that individual stimulation sites in the retina give different color perceptions, upon stimulation, then colors of the viewed scene is correlated with specific stimulation sites to provide a certain amount of color vision.

67 Claims, 8 Drawing Sheets

LOGARITHMIC LIGHT INTENSIFIER FOR USE WITH PHOTORECEPTOR-BASED IMPLANTED RETINAL PROSTHETICS AND THOSE PROSTHETICS

This application claims the benefit of U. S. Provisional Application No. 60/125,875, filed Mar. 24, 1999.

FIELD OF THE INVENTION

This invention relates generally to retinal prosthetics and more particularly to a method and apparatus for enhancing retinal prosthetic performance.

This invention relates to directly modulating a beam of photons of sufficient energy onto retinal prosthetic implants of patients who have extreme vision impairment or blindness.

BACKGROUND OF THE INVENTION

A healthy eye is has photosensitive retinal cells (e.g. rods and cones) which react to specific wavelengths of light to trigger nerve impulses. Complex interconnections among the retinal nerves assemble these impulses which are carried through the optic nerve to the visual centers of the brain, where they are interpreted. Certain forms of visual impairment are primarily attributable to a malfunction of the photosensitive retinal cells. In such cases, sight may be enhanced by a retinal prosthesis implanted in a patient's eye. Michelson (U.S. Pat. No. 4,628,933) and Chow (U.S. Pat. Nos. 5,016,633; 5,397,350; 5,556,423) teach a retinal implant, or implants, of essentially photoreceptors facing out of the eye toward the pupil, each with an electrode which can stimulate a bipolar, or similar, cell with an electrical impulse. This bipolar cell is acted upon by the electrical stimulus, to send appropriate nerve impulses essentially through the optic nerve, to the brain.

This invention is postulated as a necessary complement to this type of prosthesis, because the photoreceptors do not appear to be sensitive enough to the ordinary levels of light entering the eye in that not enough current is produced to sufficiently stimulate the retinal cells. Consequently, a light amplifier, or "helper" device would be needed. That device is the invention herein described, which also includes special characteristic implants.

Furness, et al. teach a "virtual retinal display", U.S. Pat. No. 5,659,327, where "The virtual retinal display . . . utilizes photon generation and manipulation to create a panoramic, high resolution, color virtual image that is projected directly onto the retina of the eye . . . there being no real or aerial image that is viewed via a mirror or optics." Richard, et al. teach, U.S. Pat. No. 5,369,415, ". . . a direct retinal scan display including the steps of providing a directed beam of light, modulating the beam of light to impress video information onto the beam of light, deflecting the beam in two orthogonal directions, providing a planar imager including an input for receiving a beam of light into the eye of an operator which involves a redirection diffractive optical element for creating a virtual image from the beam of light on the retina of the eye, and directing the beam of light scanned in two orthogonal directions and modulated into the input of the planar imager and the output of the planar imager into the eye of an operator."

Sighted individuals can use these devices above for their intended uses. However, they appear unsuitable for use by blind individuals with implanted retinal prosthetics of the photoreceptor-electrode kind. It would seem that they do not provide enough light power. Moreover, light amplitude cannot be arbitrarily increased because according to Slinly and Wolbarscht, *Safety with Lasers and Other Optical Sources*, the retinal threshold damage is 0.4 Joules per square centimeter.

SUMMARY OF THE INVENTION

The present invention is directed to a method and apparatus for providing enhanced retinal prosthetic performance. More particularly, the invention is directed to a light amplifier and electrical circuitry for driving an implanted retinal prosthesis to maximize electrical stimulation of the retinal nerves or cells, while avoiding damage thereto. The invention is also directed to improved implanted retinal prostheses, which maximize the advantages of the light amplifier.

In accordance with one aspect of the invention, light reflected from a viewed image (i.e., input image) is passed through a light amplifier to produce an output image which is applied to the photoreceptor array of a retinal prosthesis. The gain (or "transfer function") of the light amplifier enables the photoreceptor array to drive output electrodes for producing retinal nerve impulses of sufficient magnitude to enhance perceived sight.

In accordance with another aspect of the invention, the light amplifier preferably compresses the range of light intensity, e.g., logarithmically, to enable maximum light amplification without overdriving the prosthetic photoreceptors.

In accordance with another aspect of the invention, the electrical stimulation of the retinal nerves is preferably pulsed, i.e., periodically interrupted to avoid any damage attributable to peak magnitude electrical signals. Periodic interruption can be implemented mechanically by a shutter periodically interrupting the light incident on the photoreceptor array and/or electrically via an appropriate wave shaping circuit.

In accordance with another aspect of the invention, the implanted prosthetic's electrodes generate a sequence of positive and negative pulses to avoid producing a net charge in the eye. Successive pulses are preferably spaced in time by an interval $\Delta t$.

Four preferred embodiments are described. In accordance with the first embodiment of the invention a single wavelength is relied upon to activate a combined photodetector-electronics-electrode implanted unit which then produces a negative pulse, followed by a time delay, followed by a positive pulse. A photoreceptor implanted in the eye acts to produce an electrical stimulation with an equal amount of positive and negative charge. A single light wavelength is received by the photoreceptor. That single wavelength contains extractable energy. It also contains information, which may be encoded by amplitude modulation, frequency modulation, phase shift methods or pulse width modulation, for example. The photoreceptor activates an electrode with associated electronics. The electronics produces a negative pulse followed by a time delay followed by a positive pulse. A net charge of zero is introduced into the eye by the electrode-originating electrical pulses. The preferred delay time is in the range 0.1 millisecond to 10 milliseconds, with the delay time of 2 milliseconds is most preferred. When the retinal cell is not being electrically stimulated, it returns to a rest and recovery state. It is then in a state, electrically, that it was in prior to stimulation by the first electrical stimulation.

In accordance with the second embodiment, a first wavelength is used to stimulate a first set of "electronic" photoreceptors. These photoreceptors are connected so that the stimulation of the attached, or associated, electrodes results in a negative pulse. This negative pulse provides retinal cell stimulation. Then the shutter cuts in and stops light transmission to the eye. The retinal cell is in a rest and recovery state so that it returns, electrically, to the state it was in prior to stimulation by the first particular wavelength of light. A second particular wavelength of light then stimulates a second set of photoreceptors which are sensitive to that wavelength of light; while the first set of photoreceptors are not affected. This second set of photoreceptors is connected so that the stimulation of the attached, or associated, electrodes results in a positive pulse. The net charge introduced into the retinal cells must balance. So the positive charge introduced by the positive pulse must equal the negative charge introduced by the negative pulse. Again, the shutter cuts in and stops light transmission. Again, the retinal cells rest and recover and the process repeats. An aspect of the second embodiment is using an electro-optic, electronic or mechanical shutter to provide a period of no electrical stimulation to the retinal cells targeted for electrical stimulation.

In accordance with a third embodiment, which is a cross, so to speak, between the first and second embodiments two different wavelengths and two different types of diodes, each responsive to a corresponding wavelength are used. In this embodiment, one wavelength is used to pump in a high constant level of light to supply power to the electronics component. The other wavelength is used to send in information via amplitude, frequency, phase, pulse-width modulation, or combinations thereof. The stimulation pulse from the electronics to the electrode to the retinal cell is generated in a fashion similar to the pulses generated in the first embodiment, with a single wavelength.

A fourth embodiment is that of the logarithmic light amplifier itself, without any special implantable photoreceptors. This last embodiment may require a low duty cycle when used with photoreceptors connected to a diode without any electronics. It may be able to rely sufficiently upon the intrinsic capacitance of an oxidizable electrode, which acquires capacitance with the buildup of an insulating oxidized layer toward the ionizable fluid present in the eye as vitreous fluid, or fluid directly associated with the eye.

An image receiver with a first converter for the image, converts the image into electrical signals. The signals are amplified, basically logarithmically, so as to provide brightness compression for the patient.

An aspect of the embodiments of the invention is that an amplified electrical signal is converted by a second converter into a photon-based display; the photons of this display enter an eye through the pupil of the eye. Moreover, while the embodiments of the logarithmic amplifier invention have sufficient output light power, advantageously, the output light level still remains at a safe level. This aspect of the invention corresponds to aspects of the action of the iris, as well as the biochemistry of retinal cells, in the human eye in making possible sight over many orders of magnitude of ambient brightness.

An aspect of the embodiments of the invention is incorporation of both optical and electronic magnification of the image, as for example, the incorporation of an optical zoom lens, as well as electronic magnification. Consequently, it is feasible to focus in on items of particular interest or necessity.

With proper adjustment, proper threshold amplitudes of apparent brightness would obtain, as well as comfortable maximum thresholds of apparent brightness. Therefore, to adjust for these, an adjustment aspect is incorporated in each embodiment, such that proper adjustment for the threshold amplitudes and maximum comfortable thresholds are made.

Another aspect of the invention, which may be incorporated in all embodiments, is oriented toward making color vision available, at least to a degree. To the extent that individual stimulation sites (e.g., retinal cells generally, bipolar cells specifically) give different color perceptions upon stimulation, the color of selected pixels of the viewed scene is correlated with a specific photoreceptor-electronics-electrode units located so as to electrically stimulate a specific type of bipolar cell to provide the perception of color vision.

In order to help implement both comfortable adjustment of threshold and maximum brightness, and color vision, the logarithmic light amplifier also incorporates within itself, a data processing unit which, semi-autonomously, cycles through the various photodetector-electrode and combinations thereof, interrogates the patient as to what the patient sees, the patient then supplies the answers, setting up proper apparent brightness, proper apparent color and proper perception. This setup mode is done by the use of a keyboard, display, and auxiliary processor, which are plugged into the data processing unit of the logarithmic light amplifier during the setup procedure.

A scanning laser feedback is provided in different embodiments of the invention to keep the scanner laser scanning the correct locations. An imaging of the reflected scanning laser reflected back from the retinal implant is used to provide real-time feedback information, utilizing a second imager viewing into the eye and a data processor unit tied into the scanning laser scan control unit.

BRIEF DESCRIPTION OF THE DRAWINGS

The above and other features and advantages of the invention will be more apparent from the following detailed description wherein.

DESCRIPTION OF THE PREFERRED EMBODIMENTS

Figure 1:
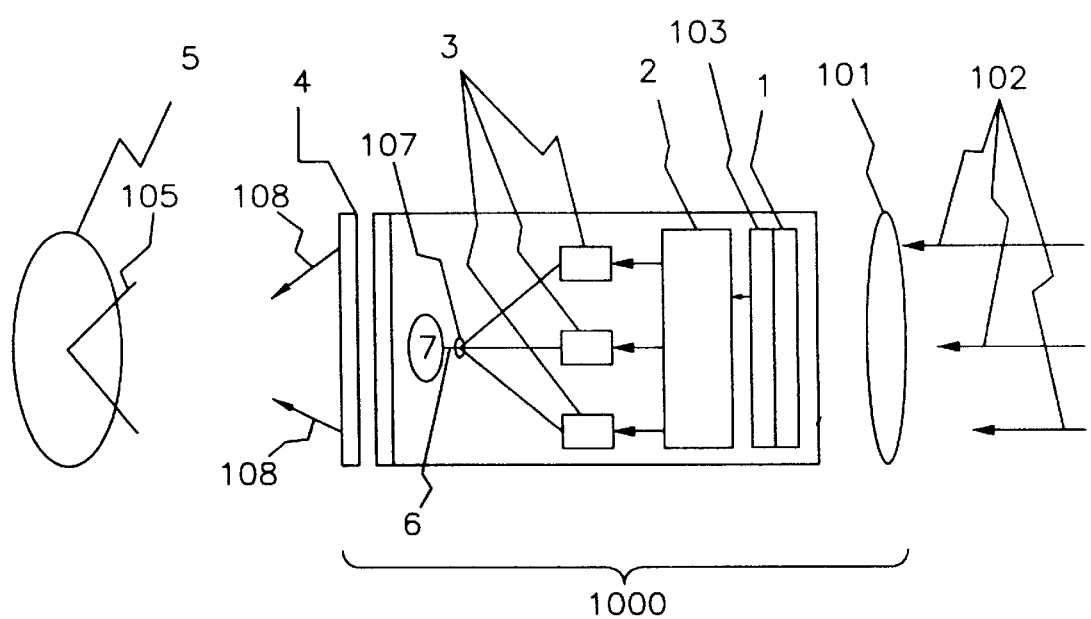
FIG. 1 shows the logarithmic light amplifier with shutter, showing the incoming scene or view photons on the right and the eye on the left.

The following description is of the best mode presently contemplated for carrying out the invention. This description is not to be taken in a limiting sense, but is merely made for the purpose of describing the general principles of the invention. The scope of the invention should be determined with reference to the claims.

This invention provides amplified light for artificial photoreceptors implanted in the eye of a patient who has lost the use of his/her normal photoreceptor retinal cells. The purpose of this amplified light is to effectively stimulate the artificial photoreceptors. The artificial photoreceptors, in turn, provide electrical stimulation through associated electrodes, usually via some electronics, to retinal cells, which are normally stimulated by living retinal photoreceptors such as cones and rods. The retinal cells, which get electrically stimulated by way of the artificial photoreceptors, are typically bipolar cells. This stimulation to these non-photoreceptor retinal cells allows the patient to have at least some perception of what a normal eye would see. In order not to damage the retinal cells, light is fed to the photoreceptor-electrode stimulators in the following ways.

Four preferred embodiments are described. In the first embodiment a single wavelength is relied upon to activate a combined photodetector-electronics-electrode implanted unit which then produces a negative pulse, followed by a time delay, followed by a negative pulse. In the first embodiment, a photoreceptor implanted in the eye acts to produce an electrical stimulation with an equal amount of positive and negative charge. A single light wavelength is received by the photoreceptor. The photoreceptor activates an electrode with associated electronics. The electronics produces a negative pulse followed by a time delay followed by a positive pulse. A net charge of zero is introduced into the eye by the electrode-originating electrical pulses. The preferred delay time is in the range 0.1 millisecond to 10 milliseconds, with the delay time of 2 milliseconds is most preferred. When he retinal cell is not being electrically stimulated, it returns to a rest and recovery state. It is then in a state, electrically, it was in prior to stimulation by the first electrical stimulation.

Starting with the logarithmic amplifier, an image receiver with a first converter for the image, converts the image into electrical signals. The signals are amplified, basically logarithmically, so as to provide brightness compression for the patient. The amplified electrical signal is converted by a second converter into a photon-based display; wherein said photons of said display enter an eye through a pupil of said eye.

Photons (102) from a viewed scene (not shown) enter the logarithmic amplifier (1000) by way of the lens (101). The light amplifier (1000) has an image receiver (1), a first converter (103) of the image into electrical signals, an amplifier (2) of said electrical signals whereby the overall amplification of said electrical signal according to a definite functional relationship between input signal to the amplifier and an output signal from the amplifier, a second converter (107) of said amplified electrical signal into a photon-based display (7); such that the of display photons (108) enter an eye (5) through the pupil (105) of the eye (5). In the case where the imager (1) is a type of video camera, the image receiver and conversion to electrical signals may occur in a package (old in the art).

A display (7) that is a source of photons such as a laser (coherent light source) (7), or a non-coherent source such as colored LEDs (7), or a plasma display (7), is used to send photons directly to an implant near the retina. These displays (7) are made very bright, but not such as to impact negatively on the eye. In our cases, the patient has sufficient retinal degeneration so as to be unable to see without the aid of a retinal prosthetic. In the case where the display (photon source) is a laser (7), that laser is scanned over the implanted photodetector-electronics-electrode array (FIG. 2, (8) in accordance with the scene being displayed to the eye. A scanning laser is a laser with scanning means (old in the art).

Figure 2A:
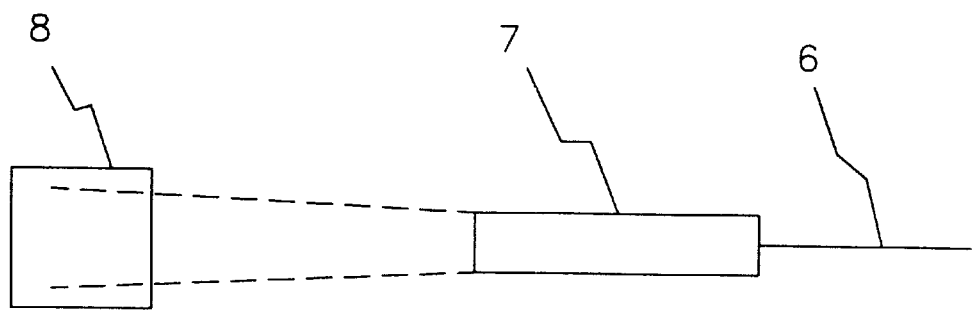
FIG. 2a shows a laser being modulated by a video signal and scanning the full extent of the implanted retinal prosthesis.
Figure 2B:
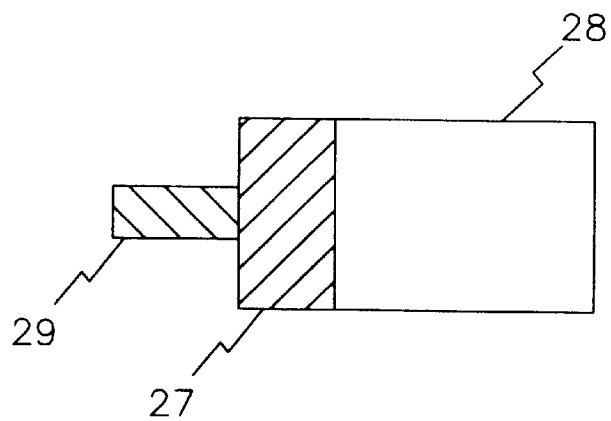
FIG. 2b shows a photoreceptor, associated electronics, and an associated electrode.
Figure 2C:
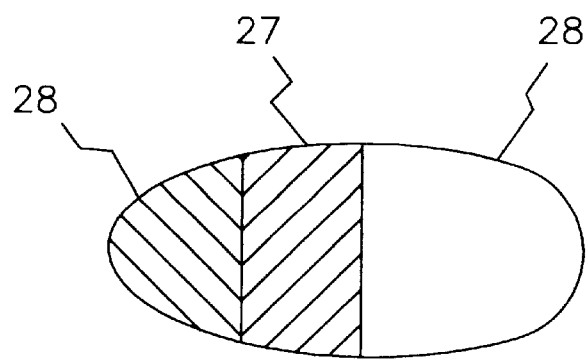
FIG. 2c shows the apparatus of FIG. 2b but in a more rounded, smoother packaged form, likely more amenable for implantation into the eye.

Referencing FIG. 2a, the video signal (6) is applied to a scanning laser (7), a scanning laser being a laser with scanning means (old in the art). The scanning laser (7) is scanned over the retinal prosthesis in a square or rectangular pattern or in a raster pattern with an exact fit to the prosthesis (8). The video signal (6) supplies amplitude from the data processor (FIG. 1, (2)), and if desired (see FIG. 1), color information, of the scene being viewed, from the individual color amplifiers (3) to the laser (7), which information is used to modulate the laser.

Figure 4:
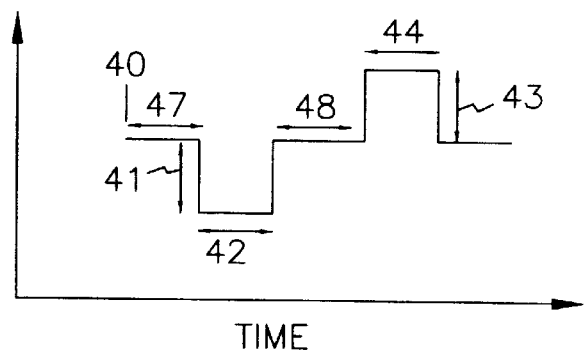
FIG. 4 shows a sample waveform possible with the apparatus shown in FIG. 3.

In a preferred mode, the light amplifier (1000) is a logarithmic amplifier. In another preferred mode, the amplifier amplifies according to a different function than the logarithmic function or a modified logarithmic function, for example, an algebraic function such as a polynomial function multiplied by the logarithmic function The imager or camera lens is shown schematically as (101). The signal is logarithmically amplified as a whole at the electronic processor (2), or the individual RGB (red, green, blue) or RGBY (red, green, blue, yellow) color components are individually logarithmically amplified (3). Another color component mix of white light may be used. The individual amplification (3) of separate color components allows for the relative super-amplification of one color to which the photoreceptors are particularly sensitive. If only a "black-and-white" contrast image is displayed, the "white" part of that image is logarithmically translated to the color, i.e., wavelength, to which the photoreceptors are most sensitive. This feature includes shifting the wavelength toward or to the near infrared or toward or to the near ultraviolet, according to what is needed to optimize the response of the implanted photosensitive elements. Consequently, a mapping of the incoming image data to an appropriate output is possible. This mapping could be complex, for example, producing biphasic waveforms as shown in FIG. 4 by appropriate timing of two lasers operating at different wavelengths and photosensitive elements uniquely sensitive to these wavelengths.

In a preferred mode, individual RGB (red, green, blue) or RGBY (red, green, blue, yellow) color components are amplified separately (3), or amplified together (2) and separated out (3) after the amplification. These color components may be used to stimulate particular photosensitive elements of the retinal implant(s). For example, a cell ("blue-sensation") producing a sensation of blue color is stimulated when the scene being transmitted to the eye has blue, which in the projected (into the eye) scene would have blue in the vicinity of that blue-sensation cell.

The logarithmic amplification is necessary to compress the range of original brightness. The normal eye does this automatically of closing down the pupil size, squinting and employing other electrochemical cellular mechanisms. This light amplifier accomplishes this necessary task by electronic logarithmic light amplification. The light amplifier also includes an adjustable transformer or magnification of image size. A shutter or electronically turning the scanning laser on and off are not a necessary part of this embodiment.

In the second preferred embodiment of the light amplifier two or more wavelengths are used to communicate light energy to the eye to allow balanced biphasic stimulation with no net charge injection into the eye. A first wavelength is used to stimulate a first set of photoreceptors. These photoreceptors are connected so that the stimulation of the attached, or associated, electrodes results in a negative pulse. This negative pulse provides retinal cell stimulation. Then the shutter cuts in and stops light transmission to the eye. The time of this light interruption is preferred in the range 0.1 millisecond to 10 milliseconds, with the time of 2 milliseconds most preferred. The retinal cell is in a rest and recovery state so that it returns, electrically, to the state it was in prior to stimulation by the first particular wavelength of light. A second wavelength of light then stimulates a second set of photoreceptors which are sensitive to that wavelength of light; while the first set of photoreceptors are not affected. This second set of photoreceptors is connected so that the stimulation of the attached, or associated, electrodes results in a positive pulse. The net charge introduced into the retinal cells must balance, or equal, the net charge introduced by the negative pulse. Again, the shutter cuts in and stops light transmission. Again, the retinal cells rest and recover and the process repeats.

Figure 3A:
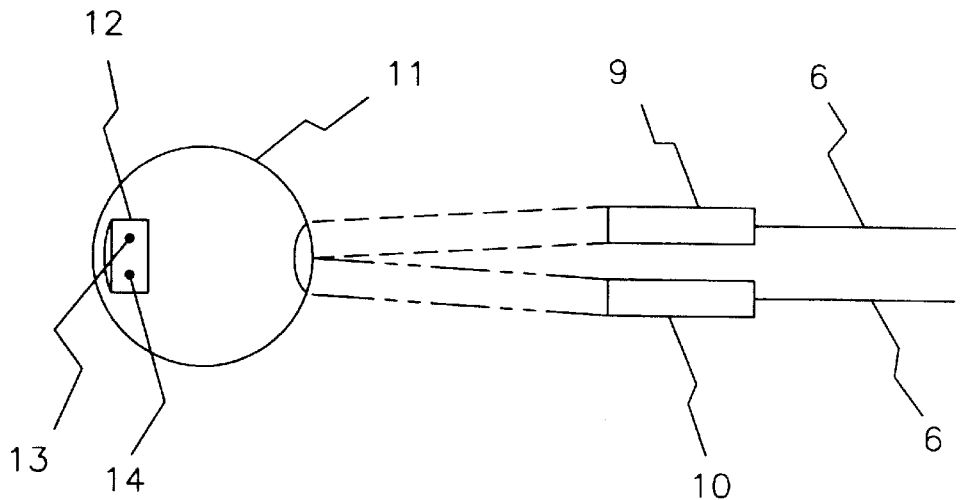
FIGS. 3A and 3B depicts tuned photodetectors on an implanted retinal prosthesis.
Figure 3B:
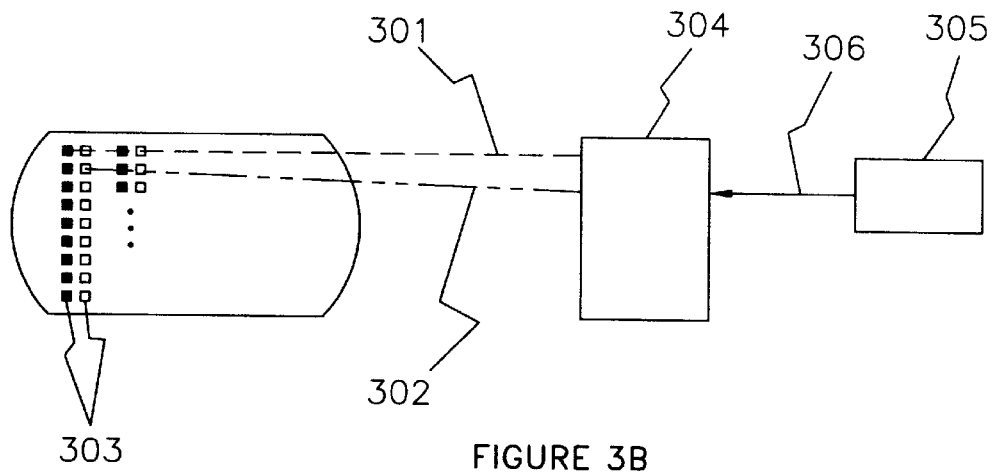

In the second preferred embodiment, FIG. 3A, two scanning lasers, (9) and (10), are supplied with video signals, with each laser operating at a different wavelength. Advantageously, two or more photoreceptors (13), (14) are on the implant. The two types of photoreceptors (13), (14), are tuned to different frequencies of light, each of the frequencies being that of one of the emitting frequencies of the external lasers (9), (10). FIG. 3B shows two incoming frequencies of light, (301) and (302). The light sources for the dual light frequencies (301), (302) is a unit (304) which is downstream in the information flow from the imager (FIG. 1, (101), (1), (103)) and amplifiers (FIG. 1, (2), (3)). The final output from the amplification stages is connected electrically or electromagnetically to the dual light frequency sources (304), in particular, dual scanning lasers operating with different wavelengths of light output. Pairs (303) of different frequency (i.e., wavelength) photoreceptors are placed on the eye-implant, each pair associated with an electrode (not shown).

Together, the two types of photoreceptors (e.g., photodiodes) give rise to a biphasic current (FIG. 4) at each electrode (not shown). Initially the rest state appears (40). Next, one of the photoreceptors (13) has been activated by its corresponding laser (9). The current amplitude is negative. (41). After a time (42), laser (9) and photoreceptor (13) shut down and the amplitude returns to zero. Next, the other laser (10) actives its corresponding (in light wavelength) photoreceptor (14) and the amplitude is positive by an amount (43) and for a duration (44). Nominally, in absolute value, (41)=(43), and (42)=(44). However, in the case this is not exact, then the parameters (44) and (43) can be altered such that (41) * (42)=(43) * (44), where * indicates multiplication. This can be accomplished by measuring (41) and (42) and then altering (43) or (44) or both to maintain charge balance.

A shutter (4) is part of the second embodiment. The shutter (FIG. 1, (4)) is of a mechanical design (old in the art), or an electronic shutter (4) (old in the art) or an electro-optical shutter (4) (old in the art). The shutter (4) cuts off light from the logarithmic light amplifier (1000) to the pupil (105) of the eye (5). This decreases the total time that light strikes the photoreceptors (FIG. 3a, (13), (14)), (FIG. 3b, 303) Consequently, the time during which the bipolar, or similar cells, are stimulated is decreased. Because the eye is not functioning as originally intended, the bipolar, or similar, cells are thought to need this "down-time" to continue to function properly.

An aspect of this invention is the use of two or more wavelengths to allow balanced biphasic stimulation with no net charge injection into the eye. As long as a biphasic type of electrical stimulation, where equal amounts of positive charge and negative charge in the form of ionic carriers or electrons or other charge carriers, enter the vitreous fluid of the eye, the electrical effect on the eye is not harmful. If direct current is supplied to the eye, internally, a charge imbalance results. This excess of charge has been found to be harmful to cells. Consequently, direct current can harm the bipolar and other cells. Advantageously, the biphasic electrical stimulation tends to avoid this harm to the cells because no excess charge accumulates.

A third embodiment that is a cross, so to speak, between the first and second embodiments uses two different wavelengths and two different types of diodes, each responsive to a corresponding wavelength. In this embodiment, one wavelength is used to pump in a high constant level of light to supply power to the electronics component. The other wavelength is used to send in information via amplitude, frequency, phase, pulse-width modulation, or combinations thereof. The stimulation pulse from the electronics to the electrode to the retinal cell is generated in a fashion similar to the pulses generated in the first embodiment, with a single wavelength.

Figure 5:
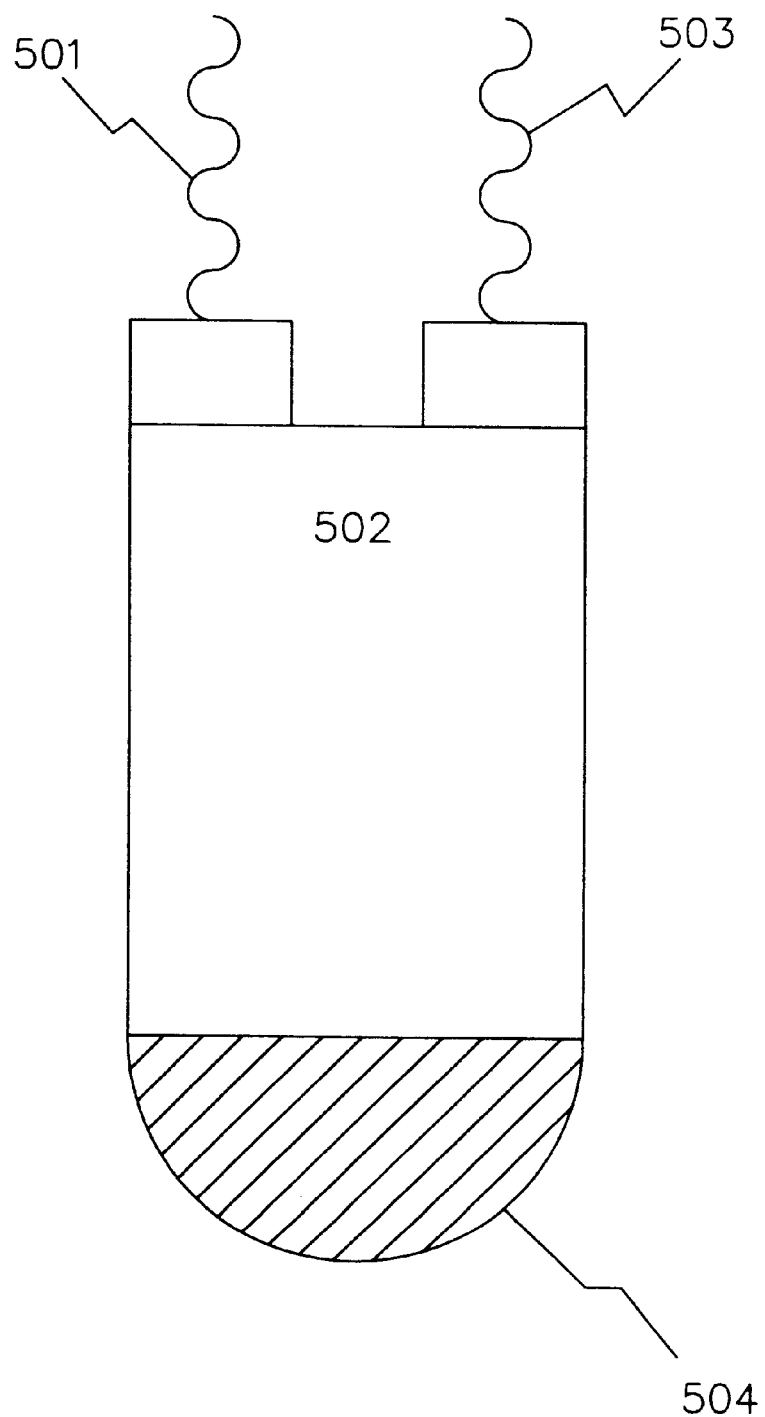
FIG. 5 shows two different wavelengths, one to send in power, the other to send in information, to a single unit with two differently sensitive photoreceptors, one electronics package and one electrode.

The third embodiment uses two different wavelengths and two different types of diodes, each responsive to a corresponding wavelength. (See FIG. 3b, (301), (302)) In this embodiment, one wavelength (FIG. 5, (501)) is used to pump in a high constant level of light to supply power to the electronics component (502). The other wavelength (503) is used to send in information via amplitude, frequency, phase, pulse-width modulation, or combinations thereof to the electronics component (502). The stimulation pulse from the electronics (502) to the electrode (504) to the retinal cell is generated in a fashion similar to the pulses generated in the first embodiment, with a single wavelength.

Figure 6:
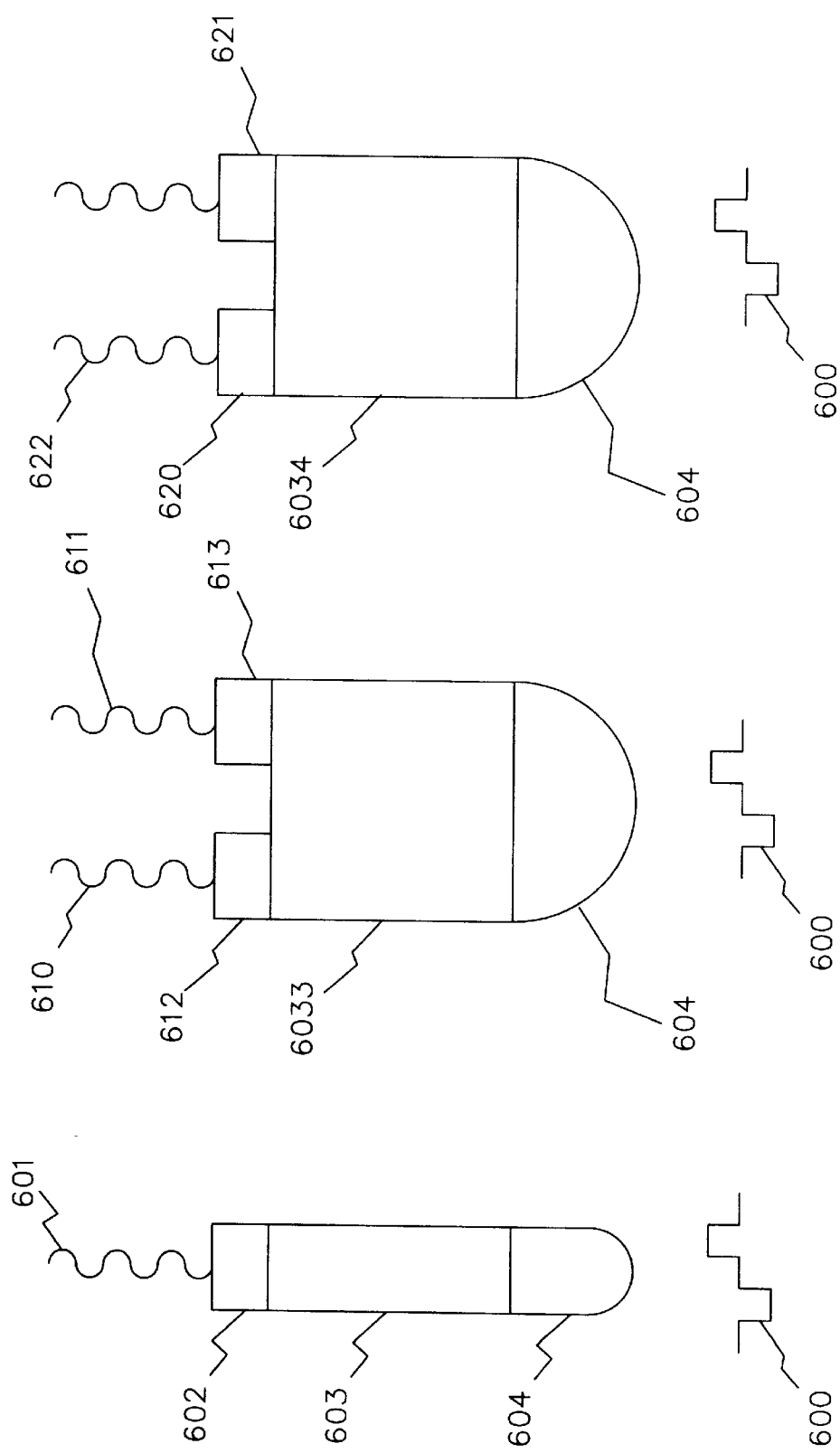
FIG. 6 summarizes three embodiments as shown previously.

See FIG. 6. FIG. 6 summarizes in block form the preceding three embodiments. In the first embodiment there is one wavelength (601) input to a single diode (602) with electronics (603) and electrode (604). Either digitally or by analogue means, old in the art, a d. c. signal occurring after the absorption of photons by the photoreceptor is converted by the electronics to a signal (600) of the type shown in FIG. 4, at the electrode. In the second embodiment, for two different wavelengths (610), (611), both carrying power and information, impinging on two different photoreceptors (612), (613), the electronics (6033), digital or analogue, again produce the waveform (600) of FIG. 4 at the electrode (604). In the third embodiment, for two different photoreceptors (620), (621), the first receiving a steady state power wavelength (622), the second receiving a signal wavelength (623), the electronics (6034), digital or analogue, produces the signal (600) of FIG. 4 at the electrode (604). The electronic circuitry of (603), (6033) and (6034) may be different.

Figure 8:
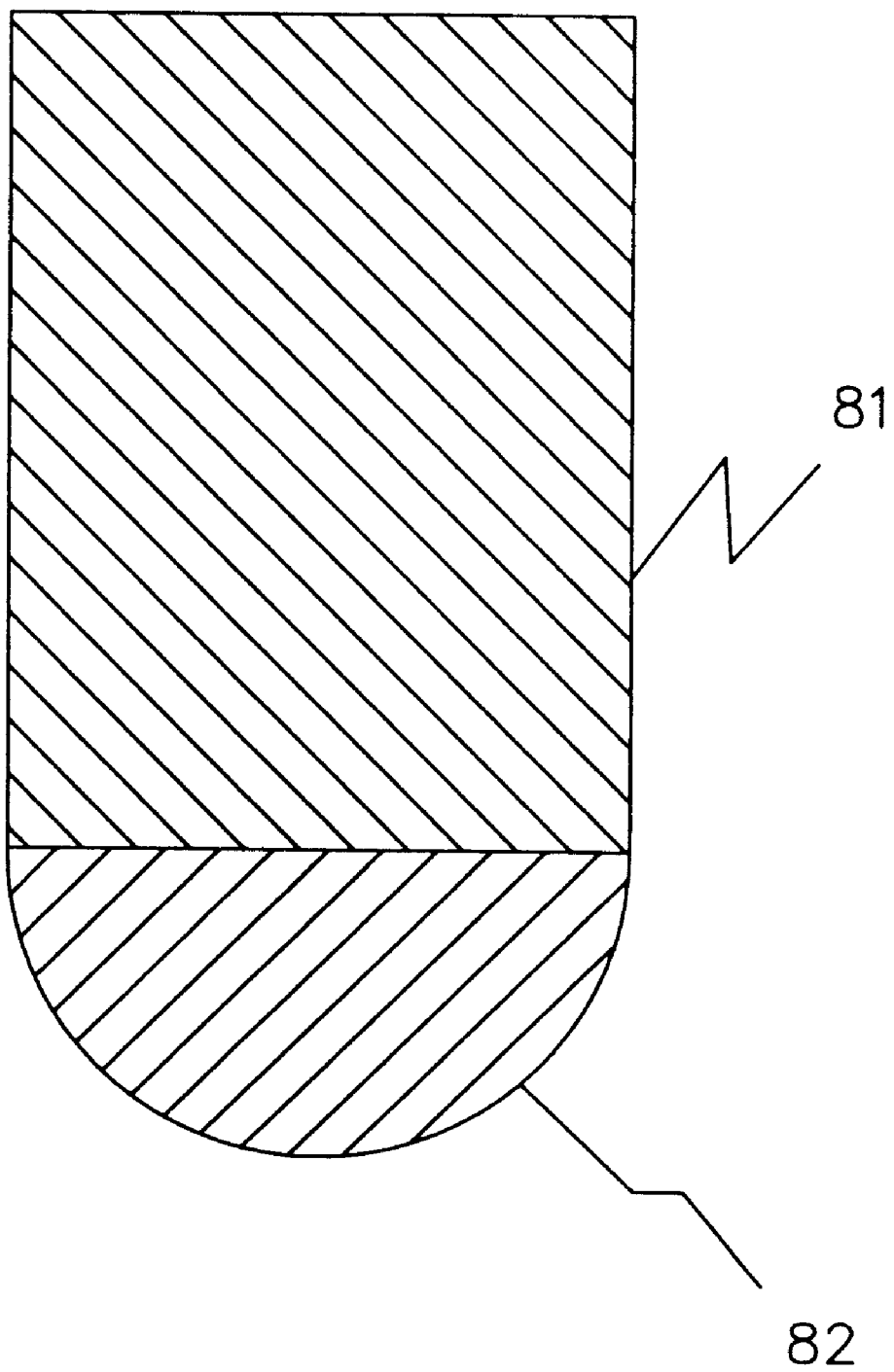
FIG. 8 shows an implant unit (old in the art) with a photoreceptor and an electrode.

A fourth embodiment is that of the logarithmic light amplifier (1000) itself, without any special implantable photoreceptors. This last embodiment may require a low duty cycle when used with photoreceptors (FIG. 8, (81)) connected to an electrode (82) without any electronics. It relies upon the intrinsic capacitance of an oxidizable electrode, which acquires capacitance with the buildup of an insulating oxidized layer toward the ionizable fluid present in the eye as vitreous fluid, or fluid directly associated with the eye.

In a first set of embodiments, the addition of a shutter (FIG. 1, (4)) with an off time of from 0.5 ms to 10 ms, most preferably 2 ms provides a mechanism to provide that off time (FIG. 4, (47), (48)). However, in a second set of embodiments, the time each laser is on can be controlled by electronic means (old in the art) within the laser to provide equal positive pulses and negative pulses, i.e., equal with respect to total signed charge introduced into a retinal cell. The first and second sets of embodiments may be completely or partially coincident.

Another aspect of all of the embodiments is incorporation of both optical and electronic magnification of the image, as for example, the incorporation of an optical zoom lens, as well as electronic magnification. Optical magnification of the image (see FIG. 1) is accomplished by use of a zoom lens for the camera lens (101). Electronic magnification is accomplished electronically in an electronic data processing unit (2) or (3). Consequently, it is feasible to focus in on items of particular interest or necessity.

With proper adjustment, proper threshold amplitudes of apparent brightness obtain, as well as comfortable maximum thresholds of apparent brightness. Therefore, to adjust for these, a sixth aspect is incorporated in all of the embodiments such that proper adjustment for the threshold amplitudes and maximum comfortable thresholds can be made.

Figure 7:
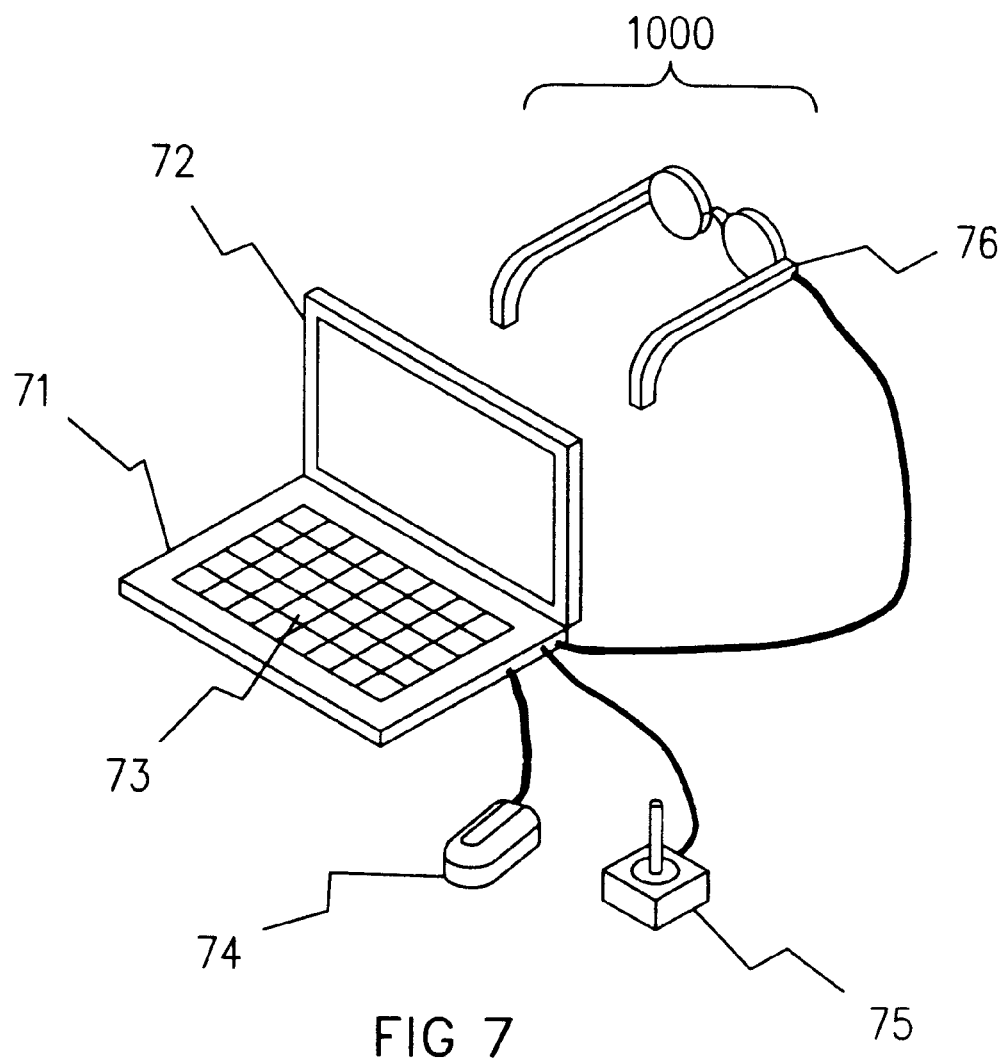
FIG. 7 shows the external logarithmic amplifier (as "glasses"), a portable computer with mouse and joystick as setup aids.

To makes color vision available, to a degree; another aspect is incorporated. To the extent that individual stimulation sites (e.g., bipolar cells) give different color perceptions upon stimulation, the color of selected pixels of the viewed scene is correlated with a specific pair of photoreceptors located so as to electrically stimulate a specific type of bipolar cell to provide the perception of color vision In order to help implement these last two aspects of the preferred embodiments of this invention, apparent brightness control and the presentment of apparent color, the logarithmic amplifier also incorporates within itself, a data processing unit which cycles electrical pulses of varying amplitude and/or frequency and/or phase and/or pulse width through the various photodetector-electrodes and spatial combinations thereof, and, interrogates the patient, who then supplies the answers, setting up proper apparent brightness and apparent color. A different aspect of the embodiments utilizes a plug in accessory data processor (FIG. 7, (71)) with display (72) and data input device or devices such as a keyboard (73), mouse (74), or joystick (75). FIG. 7 show the plug in unit (71) which plugs (76) into the logarithmic light amplifier (1000) to provide additional data processing ability as well as expanded data input and data display capability.

In order for the scanning laser to correctly scan the retinal implant prosthetic photoreceptors, it is helpful if some feedback is provided to it. One aspect of the different embodiments is the presence of a feedback loop using some of the reflected light from the scanning laser itself. One aspect of the feedback loop is to use regions of different reflectivity on the surface of the retinal implant which allow the location, or relative location, of the scanning laser light beam to be determined.

Figure 9A:
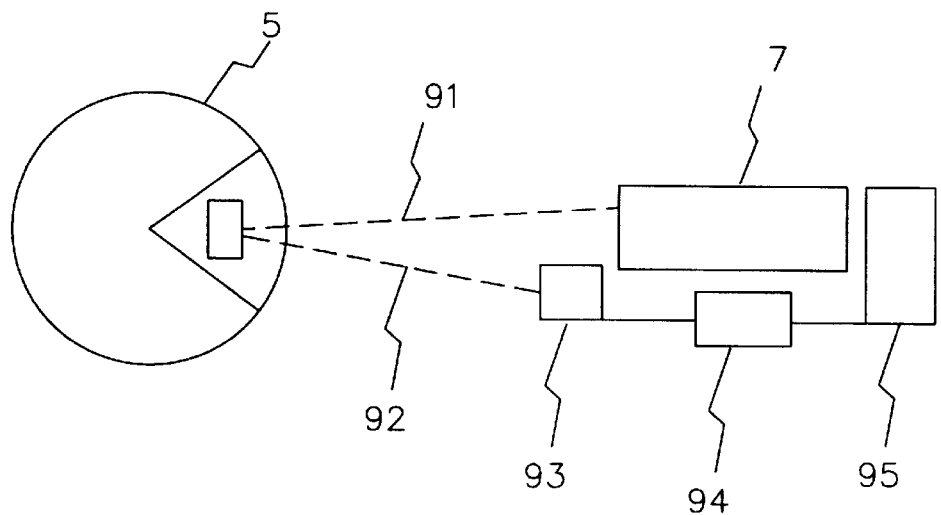
FIG. 9a shows a light-electronic feedback loop for knowing location on implant being scanned.
Figure 9B:
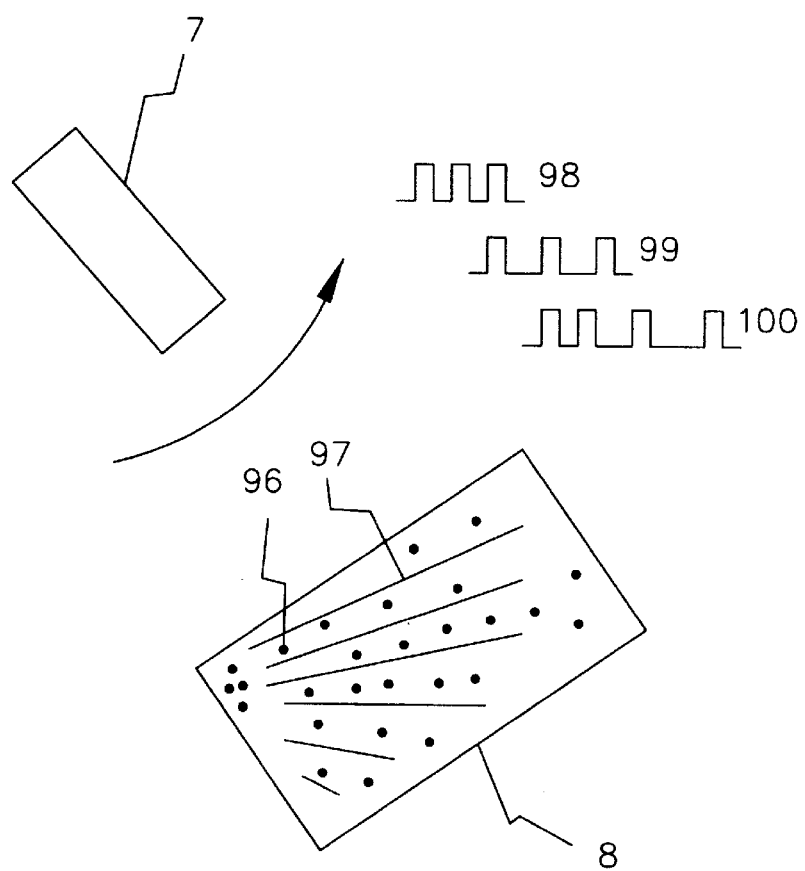
FIG. 9b shows one of different possible fiduciary markings including here points and lines for aiding knowing location on implant being scanned.

A scanning laser feedback is provided in the different embodiments of the invention. An imaging (FIG. 9a) of the retinal implant from the reflected (92) incoming scanning laser beam (91), see FIG. 9a, (7), (FIG. 1 and FIG. 2a, (7)), (FIG. 3a, (9,), (10)) reflected back from the retinal implant (FIG. 9, (8)) can be used to provide real-time feedback information, utilizing a second imager (93) viewing into the eye (5) and a data processor unit (94) tied into the scanning laser's scan control unit (95).

Another aspect of the embodiments (FIG. 9b) utilizes multiple fiduciary reflective or light absorptive points (96) and/or lines (97) on the retinal implant (8) such that the frequency and signal pattern, more generally, (98), (99), (100) of the high reflectivity from these reflective, or absorptive lines/point for a given rate of scanning by the scanning laser (7) can be used to correct the scanning direction from the different frequency patterns, some indicating correct scanning, others indicating an incorrect scanning.

While the invention herein disclosed has been described by means of specific embodiments and applications thereof, numerous modifications and variations could be made thereto by those skilled in the art without departing from the scope of the invention set forth in the claims.

What is claimed is:

1. A retinal prosthesis comprising:
   a first light receiver for collection of a received visual image;
   a light amplifier coupled to said first light receiver, amplifying said received visual image beyond incident light levels, and producing an amplified visual image;
   a light transmitter, coupled to said light amplifier, and transmitting said amplified visual image;
   a second light receiver for collection of said amplified visual image;
   a transducer, coupled to said second light receiver, for converting said amplified visual image into an electrical signal; and
   an electrode coupled to said transducer suitable for stimulating a retina.

2. The retinal prosthesis according to claim 1, wherein said light amplifier amplifies said received visual image according to a predetermined transfer function.

3. The retinal prosthesis according to claim 2, wherein said transfer function creates a logarithmic relationship between said received visual image and said amplified visual image.

4. The retinal prosthesis according to claim 2, wherein said transfer function is a logarithmic compression function.

5. The retinal prosthesis according to claim 1, wherein said light amplifier provides the necessary power to operate said second light receiver and said transducer.

6. The retinal prosthesis according to claim 5, wherein said light amplifier provides a signal comprising:
   a carrier providing power to said second light receiver and said transducer; and
   a modulated signal selected from the set of frequency modulation, pulse width modulation and phase shift modulation, and encoding said amplified visual image.

7. The retinal prosthesis according to claim 5, wherein said necessary power is provided on a first light frequency and said amplified visual image is provided on a second light frequency.

8. The retinal prosthesis according to claim 1, further comprising control means for temporarily interrupting said amplified visual image.

9. The retinal Prosthesis according to claim 1 further comprising a size transformer of said received visual image.

10. The retinal prosthesis according to claim 9, wherein said size transformer of said received visual image is a magnifier for magnifying said received visual image.

11. The retinal prosthesis according to claim 10, wherein said magnifier is an optical zoom lens.

12. The retinal prosthesis according to claim 1, wherein said transducer produces electrical signals imposing no net charge upon the retina.

13. The retinal prosthesis according to claim 12, wherein said alternating electrical signals are biphasic pulses.

14. The retinal prosthesis according to claim 13, wherein said biphasic pulses comprises a negative pulse followed by a positive pulse.

15. The retinal prosthesis according to claim 14, further comprising control means for interrupting said signal between each positive and negative pulse.

16. The retinal prosthesis according to claim 1, wherein said light transmitter is a laser.

17. The retinal prosthesis according to claim 16, wherein said laser is a scanning laser.

18. The retinal prosthesis according to claim 17, wherein said scanning laser provides a signal comprising:
   a carrier providing power to said second light receiver and said transducer; and
   a modulated signal encoding said amplified visual image.

19. The retinal prosthesis according to claim 17, wherein said necessary power is provided on a first light frequency and said amplified visual image is provided on a second light frequency.

20. The retinal prosthesis according to claim 17, wherein said scanning laser scans said second light receiver in a raster pattern.

21. An implantable neurostimulator for stimulation of a retina comprising:
   a source of electrical stimulus;
   two or more electrodes electrically coupled to said source of electrical stimulus; and
   a oxide layer deposited on at least one of said two or more electrodes suitable for forming a capacitor when implanted in an eye.

22. The retinal prosthesis according to claim 21, further comprising an oxide layer disposed on said electrode for forming a capacitor when implanted in an eye.

23. A retinal prosthesis comprising:
   a first light receiver collecting a received visual image;
   a first transducer, coupled to said first light receiver, converting said received visual image into a first electrical signal;
   an amplifier coupled to said first transducer, amplifying said first electrical signal beyond incident light levels;
   a second transducer converting said first electrical signal to a amplified visual image;
   a light transmitter, coupled to said second transducer, and transmitting said amplified visual image;
   a second light receiver collecting said amplified visual image;
   a third transducer coupled to said second light receiver, converting said amplified visual image into a second electrical signal; and
   an electrode coupled to said third transducer suitable for stimulating a retina.

24. The retinal prosthesis according to claim 23, wherein said amplifier amplifies said first electrical signal according to a predetermined logarithmic compression function.

25. The retinal prosthesis according to claim 23, further comprising control means for temporarily interrupting said amplified visual image.

26. The retinal prosthesis according to claim 25, wherein said control means is a mechanical shutter.

27. The retinal prosthesis according to claim 25, wherein said control means is an electronic shutter.

28. The retinal prosthesis according to claim 25, wherein said control means is an electro-optical shutter.

29. The retinal prosthesis according to claim 25, wherein said amplifier amplifies a predetermined frequency more than other frequencies.

30. The retinal prosthesis according to claim 29, wherein said predetermined frequency is a frequency better received by said second light receiver.

31. The retinal prosthesis according to claim 23, further comprising a magnifier for magnifying said received visual image.

32. The retinal prosthesis according to claim 31, wherein said magnifier is an optical zoom lens.

33. The retinal prosthesis according to claim 31, wherein said magnifier is an electronic magnifier.

34. The retinal prosthesis according to claim 23, wherein said transducer produces electrical signals imposing no net charge upon the retina.

35. The retinal prosthesis according to claim 23, wherein said first light receiver is a video camera.

36. The retinal prosthesis according to claim 23, further comprising a signal processor converting signals of all frequencies to a signal on a predetermined frequency.

37. The retinal prosthesis according to claim 36, further comprising a light power source providing light on a second predetermined frequency for providing power to said second light receiver and said third light transducer.

38. The retinal prosthesis according to claim 23, further comprising a signal processor alternatively converting signals to a first predetermined frequency, followed by a second predetermined frequency, wherein signals on said first predetermined frequency result in a positive signal on said electrode, and signals on said second predetermined frequency result in a negative signal on said electrode.

39. The retinal prosthesis according to claim 38, wherein said positive signal is a pulse and said negative signal is a pulse.

40. The retinal prosthesis according to claim 23, wherein said light transmitter is a scanning laser.

41. The retinal prosthesis according to claim 40, wherein said scanning laser scans said second light receiver in a raster pattern.

42. The implantable neurostimulator according to claim 21, wherein said oxide layer prevents the flow a direct electrical current from said neurostimulator to the eye.

43. A method of improving vision comprising:
   receiving a visual image;
   amplifying said visual image beyond incident light levels;
   transmitting an amplified visual image;
   receiving said amplified visual image;
   converting said amplified visual image to an electrical signal; and
   stimulating a retina with said electrical signal.

44. The method according to claim 43, wherein said step of amplifying is carried out according to a predetermined logarithmic compression function.

45. The method according to claim 43, further comprising interrupting said amplified visual signal according to a predetermined schedule.

46. The method according to claim 43, wherein said interruption is mechanical.

47. The method according to claim 43, wherein said interruption is electro-optical.

48. The method according to claim 43, wherein said transmitting an amplified visual image is accomplished with a scanning laser.

49. The method according to claim 48, wherein said transmitting an amplified visual image is accomplished by scanning in a raster pattern.

50. The method according to claim 48, further comprising the step of altering the size of said amplified visual image.

51. The method according to claim 50, wherein the step of altering the size of said amplified visual image is magnifying said amplified visual image.

52. The method according to claim 50, wherein said step of altering the size of said amplified visual image is accomplished electronically.

53. The method according to claim 50, wherein said step of altering the size of said amplified visual image is accomplished optically.

54. A retinal prosthesis comprising:
   a light receiver for collection of a received visual image;
   an amplifier coupled to said light receiver, amplifying said received visual image beyond incident light levels in accordance with a predetermined transfer function, and producing an amplified visual image;
   a transducer, coupled to said light amplifier, for converting said amplified visual image into an electrical signal; and
   an electrode coupled to said transducer suitable for stimulating a retina.

55. The retinal prosthesis according to claim 54, wherein said predetermined transfer function is a logarithmic compression function.

56. The retinal prosthesis according to claim 54, further comprising control means for temporarily interrupting said amplified visual image.

57. The retinal prosthesis according to claim 54, further comprising a magnifier for magnifying said received visual image.

58. The retinal prosthesis according to claim 57, wherein said magnifier is an optical zoom lens.

59. The retinal prosthesis according to claim 54, wherein said transducer produces electrical signals imposing no net charge upon the retina.

60. The retinal prosthesis according to claim 54, wherein said light transmitter is a laser.

61. The retinal prosthesis according to claim 60, wherein said laser is a scanning laser.

62. The retinal prosthesis according to claim 61, wherein said scanning laser scans said second light receiver in a raster pattern.

63. The retinal prosthesis according to claim 62, further comprising:
   an alignment device receiving a reflected image of said scanning laser; and
   an alignment control device directing said scanning laser in accordance with its reflected image.

64. The retinal prosthesis according to claim 63, further comprising fiduciary marks of limited reflectivity to assist in aiming said scanning laser.

65. The retinal prosthesis according to claim 23, further comprising an oxide layer disposed on said electrode suitable for forming a capacitor when implanted in an eye.

66. The method according to claim 43, wherein said step of stimulating a retina is accomplished by an electrode having an oxide layer suitable for forming a capacitor between said electrode, said oxide layer, and an eye.

67. The retinal prosthesis according to claim 1, further comprising an oxide layer disposed on said electrode suitable for forming a capacitor when implanted in an eye.

* * * * *